(12) United States Patent
Greenfield et al.

(10) Patent No.: US 7,475,575 B1
(45) Date of Patent: Jan. 13, 2009

(54) THEFT PREVENTION SECURITY DEVICE

(76) Inventors: Jack Greenfield, 2 Irving St., Baldwin, NY (US) 11510; David B Monoson, 1530 Coolidge Ave., Baldwin, NY (US) 11510

( * ) Notice: Subject to any disclaimer, the term of this patent is extended or adjusted under 35 U.S.C. 154(b) by 30 days.

(21) Appl. No.: 11/674,033

(22) Filed: Feb. 12, 2007

(51) Int. Cl.
*E05B 73/00* (2006.01)

(52) U.S. Cl. ........................ 70/18; 70/19; 70/58; 70/62; 70/202; 211/4; 211/8

(58) Field of Classification Search .............. 211/4, 211/8; 70/14, 18, 19, 20–203
See application file for complete search history.

(56) References Cited

U.S. PATENT DOCUMENTS

| | | | | | |
|---|---|---|---|---|---|
| 924,824 | A | * | 6/1909 | Peebler | 70/15 |
| 2,668,645 | A | * | 2/1954 | Pease | 224/546 |
| 3,905,214 | A | * | 9/1975 | Bell | 70/58 |
| 4,146,242 | A | * | 3/1979 | Bose | 280/814 |
| 4,245,745 | A | * | 1/1981 | Verelle et al. | 211/8 |
| 4,300,690 | A | * | 11/1981 | Thomas | 211/4 |
| 5,060,810 | A | * | 10/1991 | Jones | 211/59.4 |
| 5,085,326 | A | * | 2/1992 | Russell et al. | 211/4 |
| 5,147,049 | A | * | 9/1992 | Schwendemann et al. | 211/70.5 |
| 5,154,072 | A | * | 10/1992 | Leyden | 70/18 |
| 5,472,101 | A | * | 12/1995 | Ahrens | 211/70.5 |
| 6,053,016 | A | * | 4/2000 | Young | 70/57 |
| 6,142,313 | A | * | 11/2000 | Young | 211/4 |
| 6,427,497 | B1 | * | 8/2002 | Mossberg et al. | 70/18 |
| 6,598,433 | B1 | | 7/2003 | Malvasio | |

* cited by examiner

*Primary Examiner*—Suzanne D Barrett
(74) *Attorney, Agent, or Firm*—Michael I. Kroll

(57) ABSTRACT

An anti-theft device for articles having some article body portion of lesser cross sectional area bounded by body portions of greater cross sectional area so that the smaller body portion can be lockably held within a passage and the larger body portions prevent removal of the article from the anti-theft device. Preferably, the anti-theft device can be used for cables and other devices having permanent non-removable enlarged sections, such as endoscopy cables.

11 Claims, 17 Drawing Sheets

THEFT PREVENTION SECURITY DEVICE

BACKGROUND OF THE INVENTION

1. Field of the Invention

The present invention relates generally to locks and, more specifically, to an anti-theft device for articles having some article body portion of lesser cross sectional area bounded by body portions of greater cross sectional area so that the smaller body portion can be lockably held within a passage and the larger body portions prevent removal of the article from the anti-theft device. Preferably, the anti-theft device can be used for cables and other devices having permanent non-removable enlarged sections, such as endoscopy cables.

The anti-theft device is comprised of a mounting portion member and a pivotal portion member that when closed forms a lockable passage section. The pivotal member has a keyed lockset and the mounting member has a lockset-lugs receiver member. Once locked a key is required to open the lock but is not required to relock the anti-theft device.

2. Description of the Prior Art

There are other security device designed for medical use. Typical of these is U.S. Pat. No. 6,598,433 issued to Malvasio on Jul. 29, 2003. While this type of security device may be suitable for the purposes for which they were designed, they would not be as suitable for the purposes of the present invention, as hereinafter described.

U.S. Pat. No. 6,598,433

Inventor: Frank A. Malvasio

Issued: Jul. 29, 2003

An anti-theft device for an endoscope, boroscope or other device is disclosed. The anti-theft device in one embodiment comprises a top portion with a channel through it and a bottom portion hingeably attached to the top portion. A locking mechanism presses the flexible tube against a resting surface. The bottom portion comprises a flange that extends into the top portion when the device is closed. A locking lip turns upon activation of the locking mechanism and extends above the flange when the device is closed, and a cam within the bottom portion pushes a bolt attached to the pressing surface upon activation of the locking mechanism, thereby pressing the flexible tube against the resting surface.

SUMMARY OF THE PRESENT INVENTION

A primary object of the present invention is to provide an anti-theft device that overcomes the shortcomings of the prior art.

A secondary object of the present invention is to provide an anti-theft device for articles having some article body portion of lesser cross sectional area bounded by body portions of greater cross sectional area so that the smaller body portion can be lockably held within an anti-theft device passage.

Another object of the present invention is to provide an anti-theft device for cables and other devices having permanent non-removable enlarged sections.

Yet another object of the present invention is to provide an anti-theft device for endoscopy cables.

Still yet another object of the present invention is to provide an anti-theft device having a mounting portion and a pivotal portion that when closed forms a lockable passage.

Another object of the present invention is to provide an anti-theft device having a keyed lockset forming an integral part of the anti-theft device pivotal portion with the mounting portion having a lockset-lugs receiver member.

Yet another object of the present invention is to provide an anti-theft device that requires a key to gain access to the lockable passage and can be relocked without the key.

Still yet another object of the present invention is to provide an anti-theft device wherein the pivotal portion has a flange that covers the mounting portion fasteners when closed.

Additional objects of the present invention will appear as the description proceeds.

The present invention overcomes the shortcomings of the prior art by providing an anti-theft device for articles having some article body portion of lesser cross sectional area bounded by body portions of greater cross sectional area so that the smaller body portion can be lockably held within a passage and the larger body portions prevent removal of the article from the anti-theft device. Preferably, the anti-theft device can be used for cables and other devices having permanent non-removable enlarged sections, such as endoscopy cables.

The anti-theft device is comprised of a mounting portion member and a pivotal portion member that when closed forms a lockable passage section. The pivotal member has a keyed lockset and the mounting member has a lockset-lugs receiver member. Once locked a key is required to open the lock but is not required to relock the anti-theft device.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which:

Referring to FIG. 1, shown is an illustrative view of the prior art;

DESCRIPTION OF THE REFERENCED NUMERALS

Figure 1:
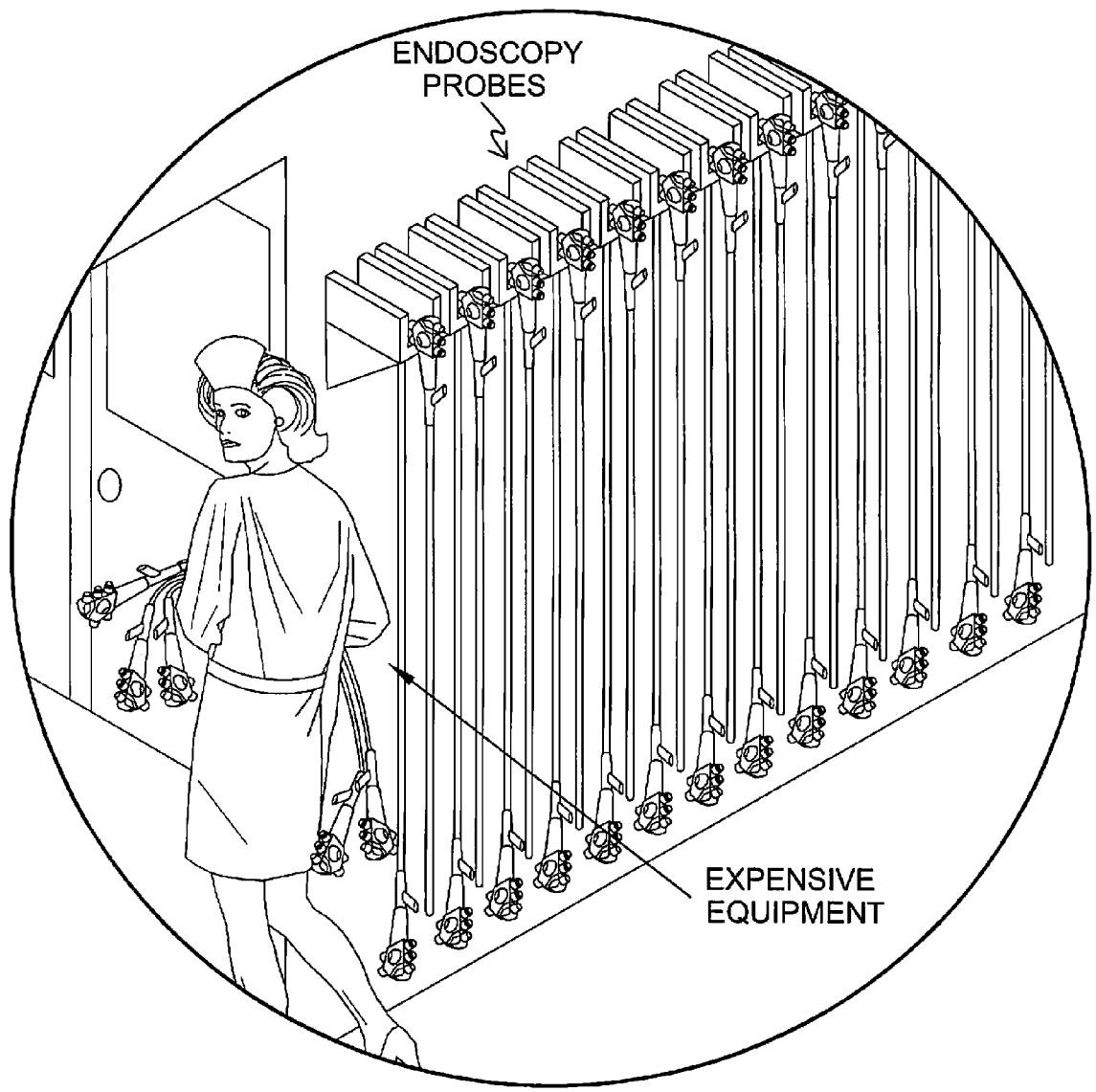

Turning now descriptively to the drawings, in which similar reference characters denote similar elements throughout the several views, the Figures illustrate the communication of the present invention. With regard to the reference numerals used, the following numbering is used throughout the various thawing Figures.

10 theft prevention security device of the present invention
12 secured article
14 lock apparatus
16 mounting plate
18 mounting plate housing
20 mounting plate fasteners
22 lock-mounting fastener apertures
24 lock stationary plate
26 stationary plate flange
28 pivot point
30 stationary plate apertures
32 lock-mounting fasteners
36 lock pivoting plate
38 lock receiver
39 lock receiver entrance aperture
40 lock receiver fastener
42 lock lug receiver
44 lock pivot-plate
46 lock pivot-plate exterior wall
48 lock pivot-plate flange
50 lock pivot-plate angle bracket
52 lock pivot-plate angle-bracket wall
54 lock pivot-plate angle-bracket plate

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

Referring to FIG. 1, shown is an illustrative view of the prior art. Depicted is the theft of easily available expensive hospital equipment that is not kept in a secure device. These thefts occur all too often at the cost of billions of dollars annually. The present invention overcomes this problem by providing a theft prevention security device for endoscopy probe cables and other devices.

Figure 2:
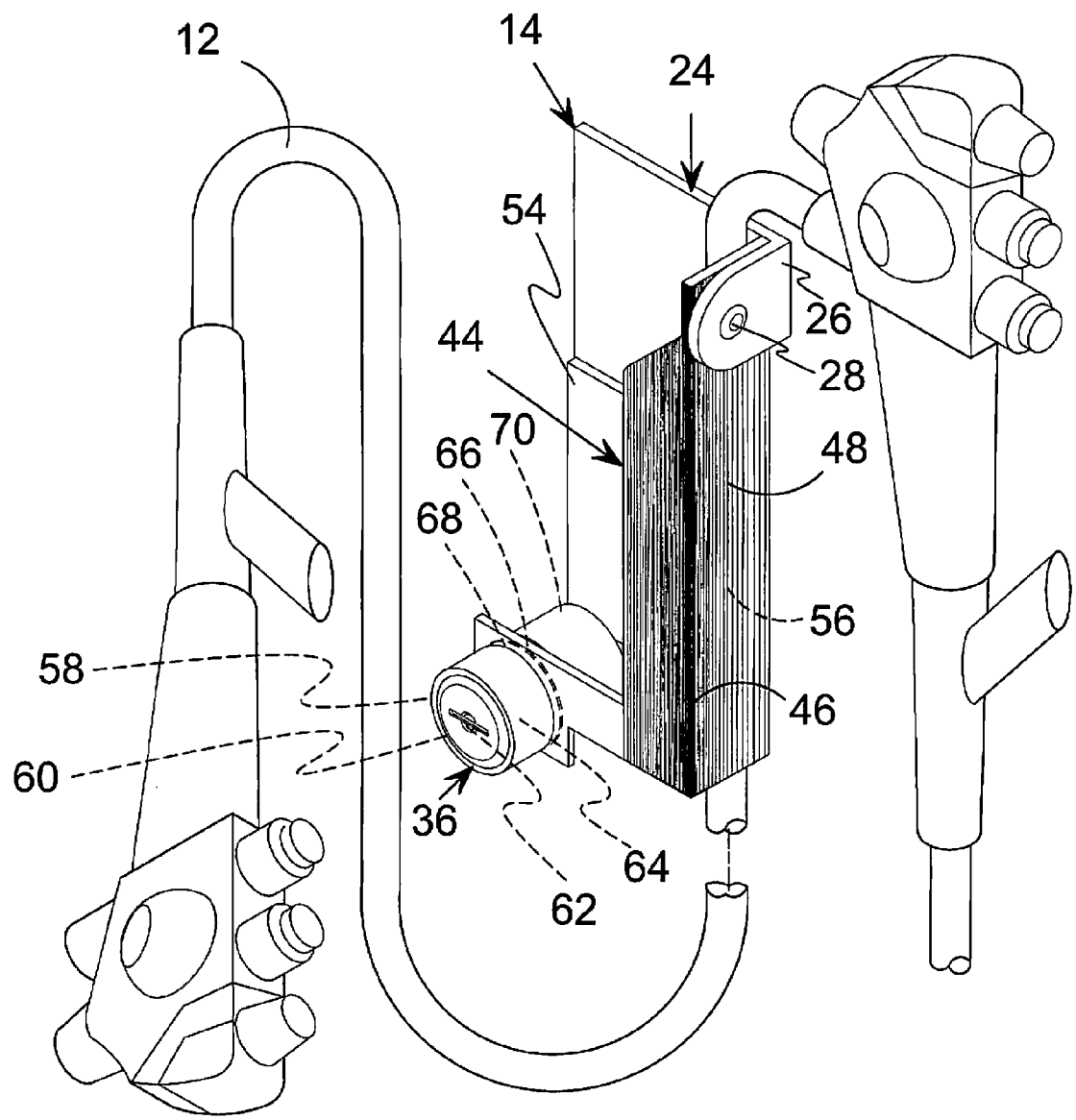
FIG. 2 is a perspective view of the present invention in a locked position.

Referring to FIG. 2, shown is a perspective view of the present invention in a locked position. Illustrated is the anti-theft security lock 10 comprising stationary plate 24 and pivot plate 44 forming a channel 56 for securing a portion of article 12 therein. Stationary plate 24 has flange 26 with a fastener passing through the flange and pivot plate forming pivot point 28. Pivot plate 44 comprises a channel formed by walls 48, 46, and 52, (shown in FIG. 5) with 52 having flange 54 that extends across the stationary plate to cover the stationary plate mounting fasteners. Lock apparatus 14 is secured to lock pivot-plate 44 by C-clip 68 inserted in C-clip channel 66 of lock cylinder 60. Once lock cylinder 60 is inserted into lock housing 58 and through pivot-plate lock aperture 64, locking lugs 70 reside in lock lug receiver 42 preventing opening of the security device 10 without a key inserted into lock-cylinder keyway 62.

Figure 3:
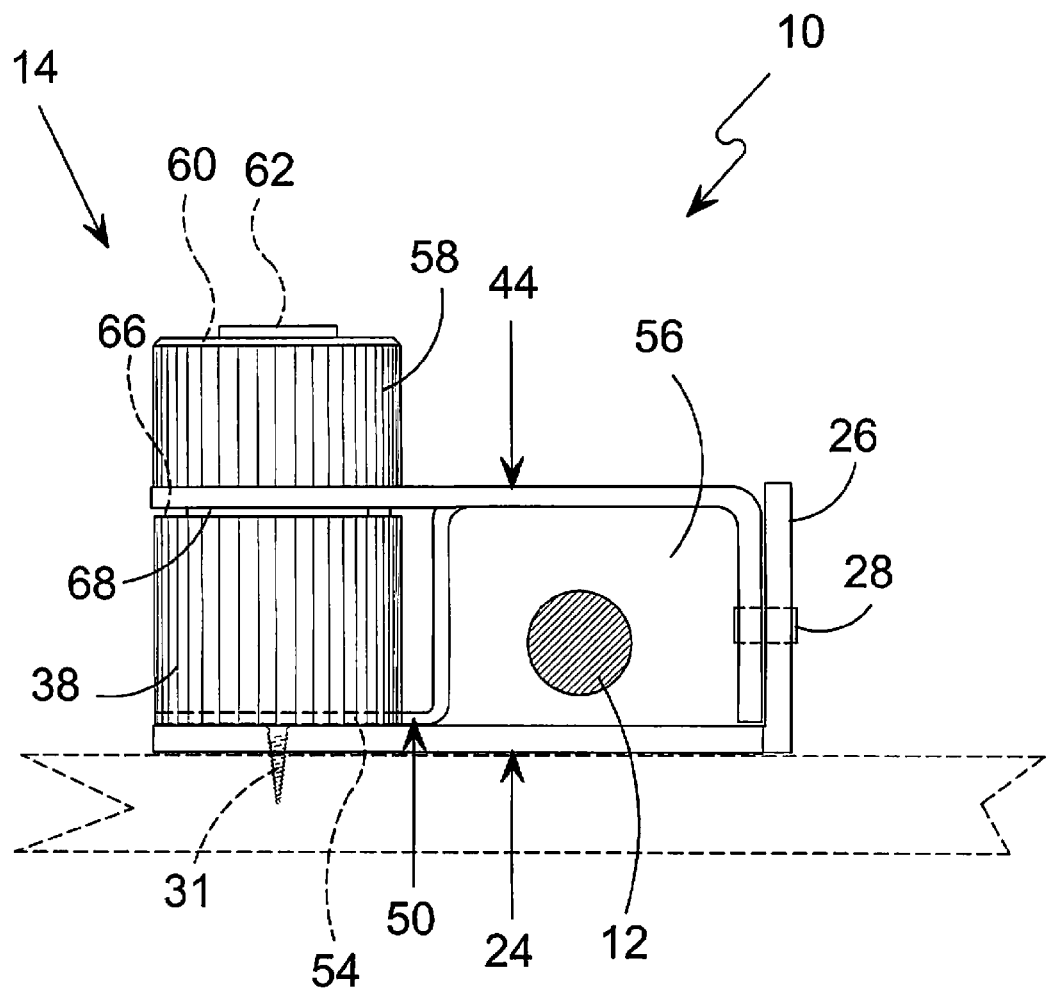
FIG. 3 is an end of the present invention with a secured article.

Referring to FIG. 3, shown is an end of the present invention with a secured article. The anti-theft security lock 10 provides locking apparatus 14 comprising stationary plate 24 and pivot plate 44 having walls forming channel 56 for securing article 12 therein. The lock receiver 38 is fastened to the stationary plate 24 and the lock housing 58 containing lock cylinder 60 and keyway 62 are secured to the pivot plate by securing the lock cylinder 60 having channel 66 to the pivot plate 44 using C-clip 68. Pivot plate 44 has flange 54, which cover stationary plate mounting fasteners 31 preventing tampering with the mounting fasteners.

Figure 4:
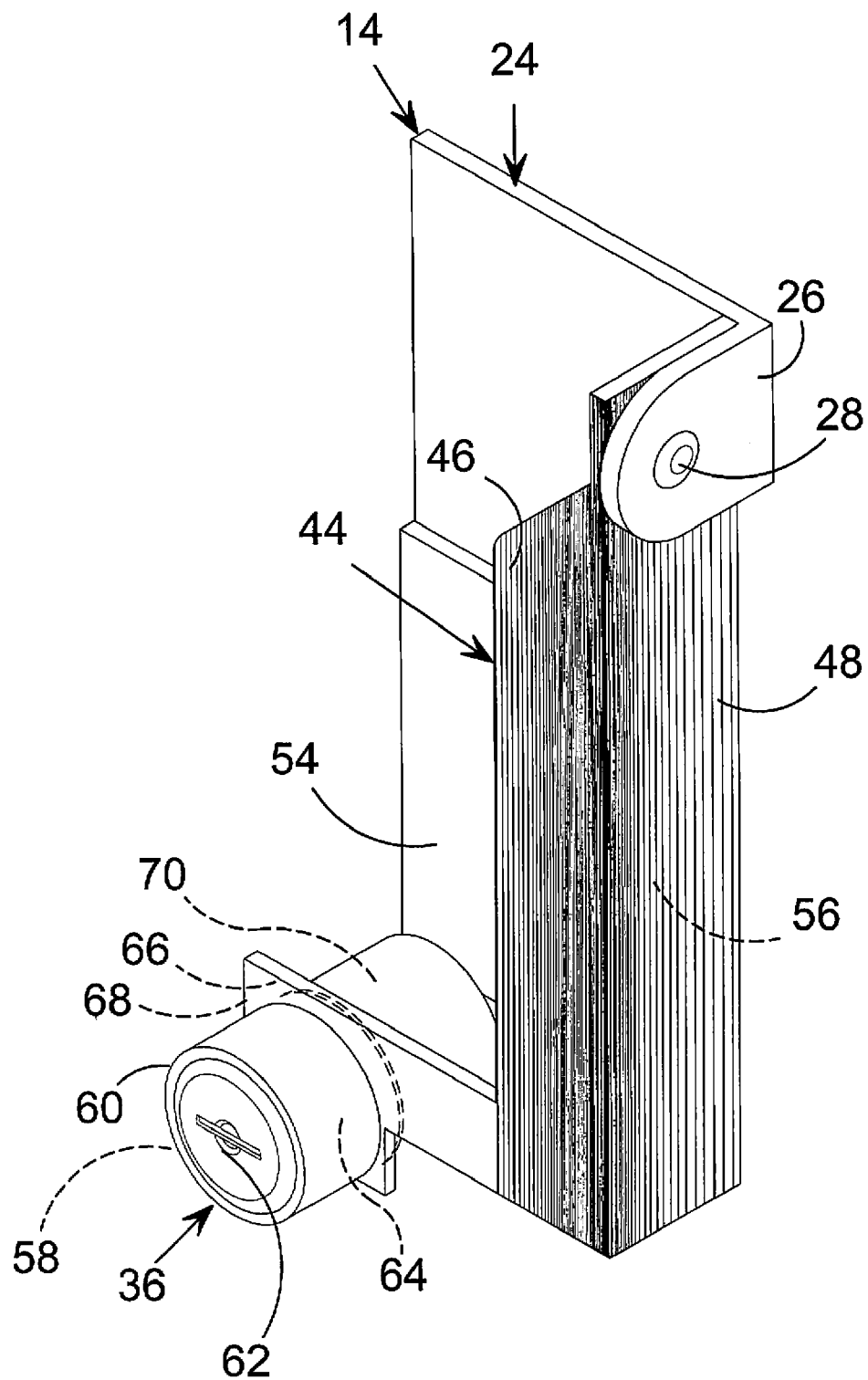
FIG. 4 is a perspective view of the present invention in a closed position.

Referring to FIG. 4, shown is the anti-theft security lock comprising stationary plate 24 having flange 26 with pivot plate 44 fastened thereto via a fastener forming pivot point 28. Also shown are the stationary plate fastening apertures 30 and lock receiver 38 fastened to the stationary plate using fastener 40 having cavity 42 for retaining lock lugs 70. The pivot plate has walls 48, 46, and 52 forming channel 56 for securing an article therein when closed. Wall 52 extends into flange 54, which will cover the stationary plate mounting fasteners when closed preventing tampering. Wall 56 has an extending leg portion with aperture 64 for receiving the lockset. The lockset comprises lock housing 56 with lock cylinder 60 positioned within. Lock cylinder 60 has a channel 66 scored into the body appropriately positioned to receive C-clip 68 once the cylinder and housing are inserted into aperture 64 and thereby secure the lockset to the pivot plate. Also shown is keyway 62 for receiving a key to open the lock.

Figure 5:
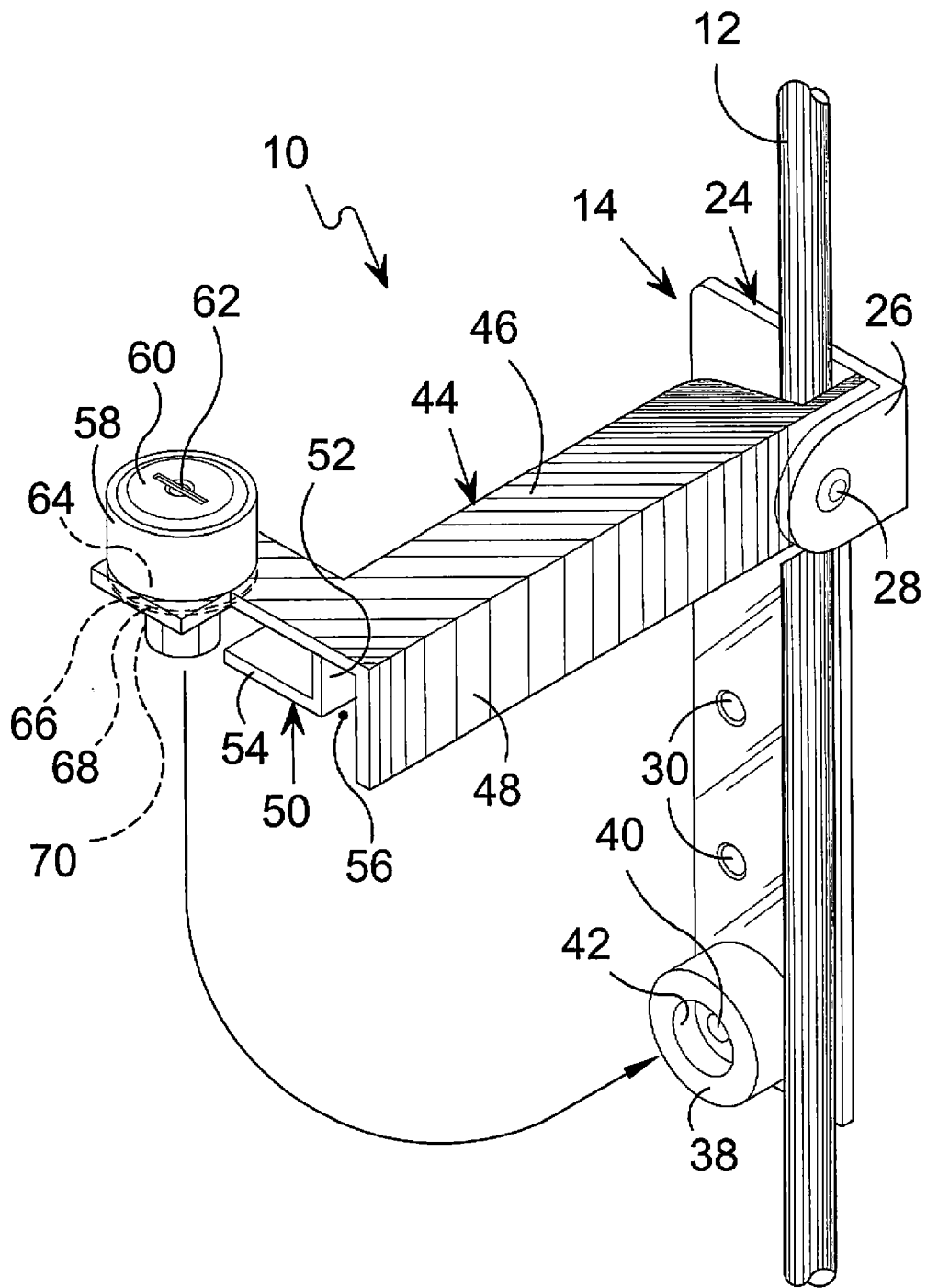
FIG. 5 is a perspective view of the present invention in an open position.

Referring to FIG. 5, shown is a perspective view of the present invention in an open position. Shown is the anti-theft security lock comprising stationary plate 24 having flange 26 with pivot plate 44 fastened thereto via a fastener forming pivot point 28. Also shown are the stationary plate fastening apertures 30 and lock receiver 38 fastened to the stationary plate using fastener 40 having cavity 42 for retaining lock lugs 70. The pivot plate has walls 48, 46, and 52 forming channel 56 for securing an article therein when closed. Wall 52 extends into flange 54 which will cover the stationary plate mounting fasteners when closed preventing tampering. Wall 56 has an extending leg portion with aperture 64 for receiving the lockset. The lockset comprises lock housing 56 with lock cylinder 60 positioned within. Lock cylinder 60 has a channel 66 scored into the body appropriately positioned to receive C-clip 68 once the cylinder and housing are inserted into aperture 64 and thereby secure the lockset to the pivot plate. Also shown is keyway 62 for receiving a key to open the lock.

Figure 6:
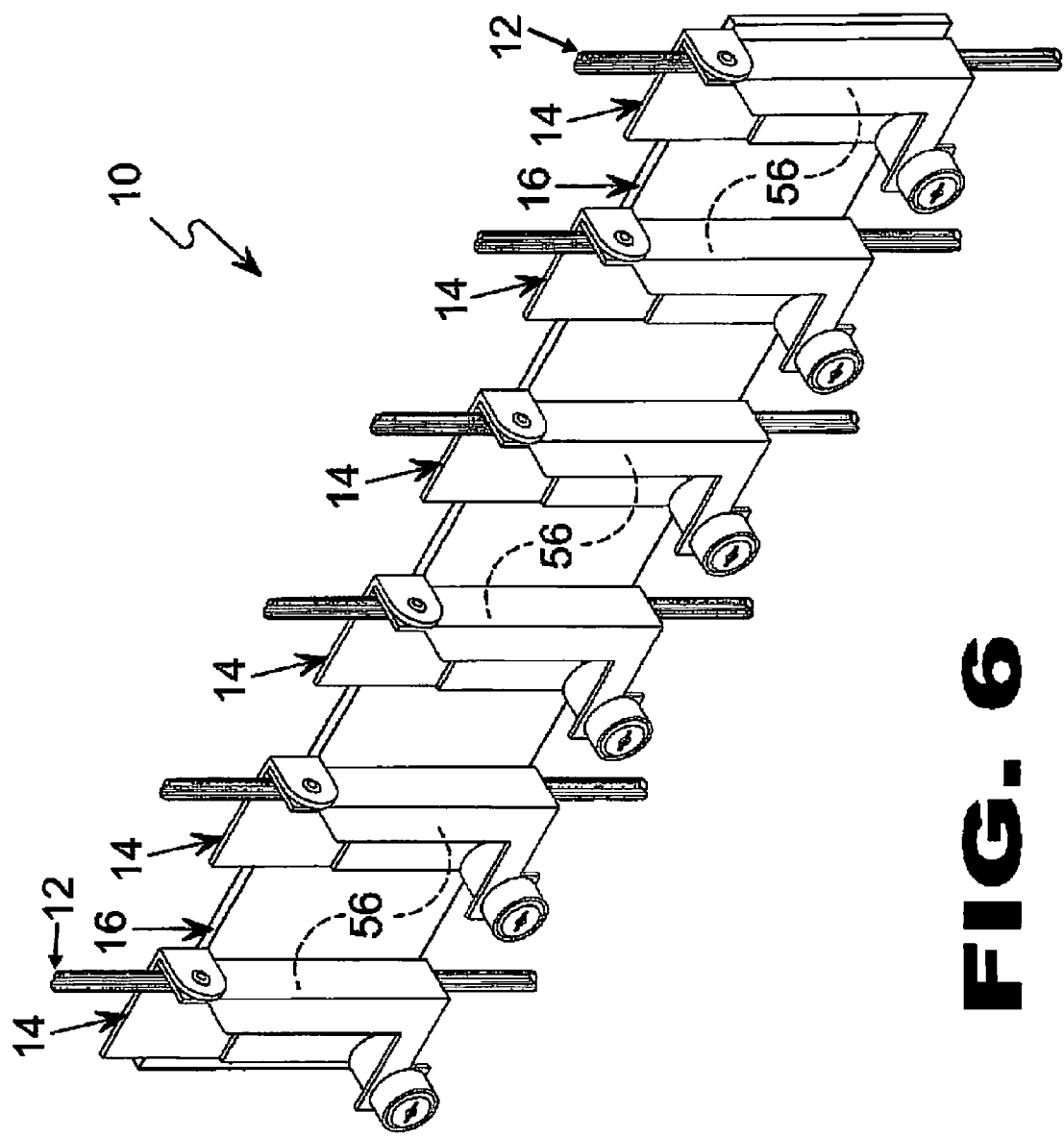
FIG. 6 is a perspective view of the present invention.

Referring to FIG. 6, shown is a perspective view of the present invention. Shown are a plurality of anti-theft security locks 14 fastened to mounting plate 16 with each security lock 14 having channel 56 for securing an article 12 therein.

Figure 7:
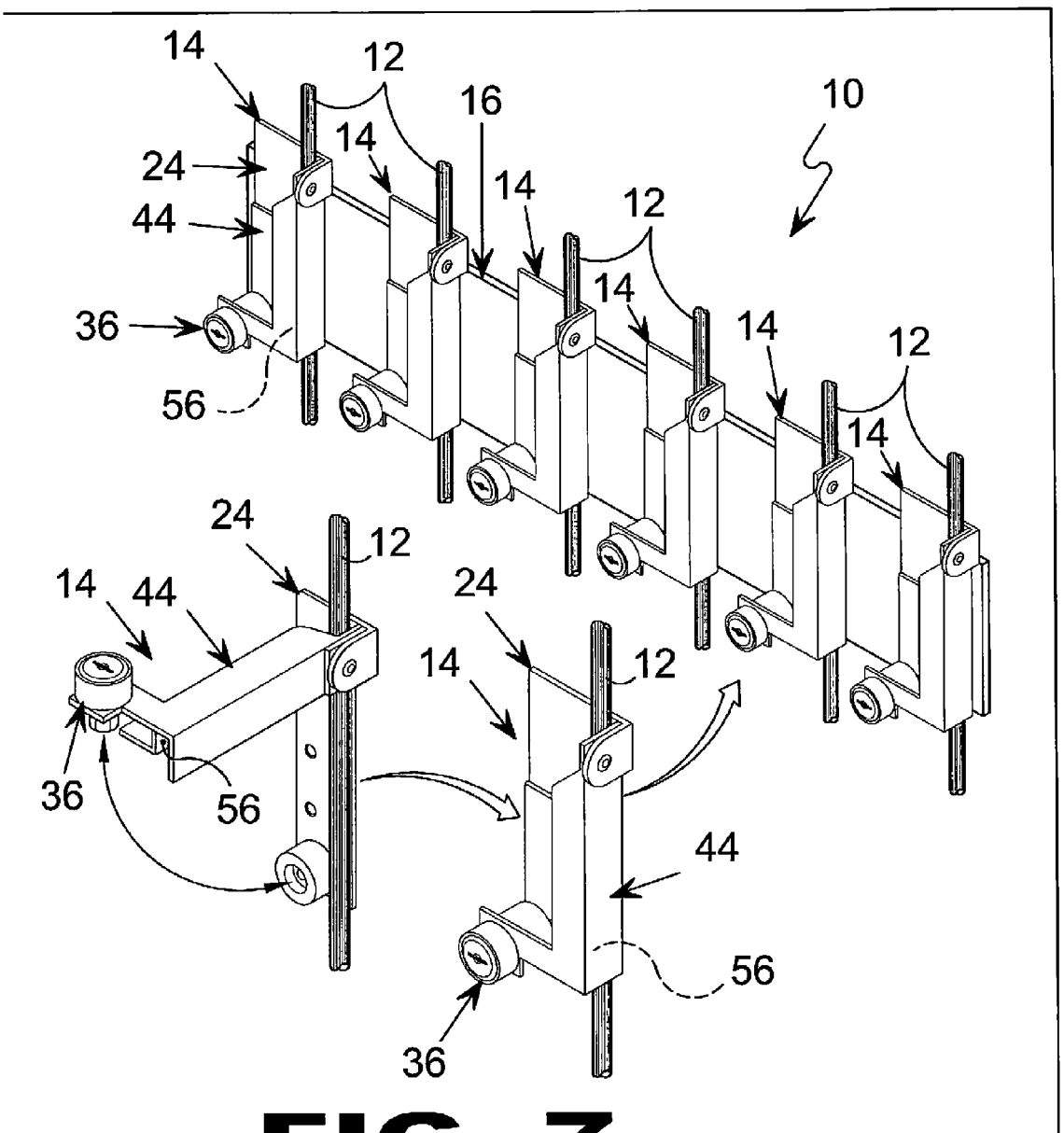
FIG. 7 is an illustrative view of the present invention in use.

Referring to FIG. 7, shown is an illustrative view of the present invention in use. Shown are a plurality of anti-theft security locks 14 fastened to mounting plate 16 with each security lock 14 having channel 56 for securing an article 12 therein.

Figure 8:
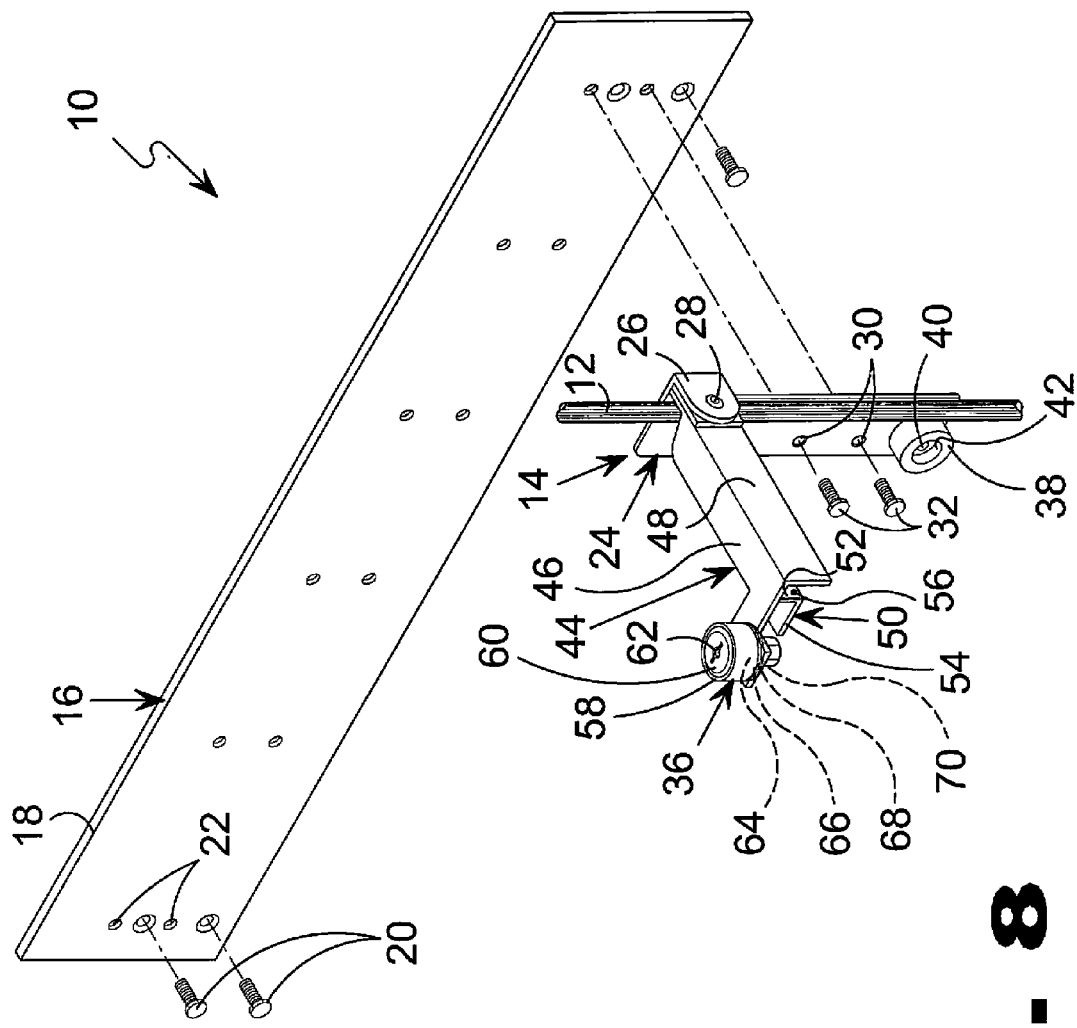
FIG. 8 is an exploded view of the present invention.

Referring to FIG. 8, shown is an exploded view of the present invention. Shown is the anti-theft security lock about to be fastened to mounting plate 16 having mounting fasteners 20 for securing the plate to structure. the lock apparatus 14 comprising stationary plate 24 having flange 26 with pivot plate 44 fastened thereto via a fastener forming pivot point 28. Also shown are the stationary plate fastening apertures 30 with fasteners 32 and lock receiver 38 fastened to the stationary plate using fastener 40 having cavity 42 for retaining lock lugs 70. The pivot plate has walls 48, 46, and 52 forming channel 56 for securing an article therein when closed. Wall 52 extends into flange 54 which will cover the stationary plate mounting fasteners when closed preventing tampering. Wall 56 has an extending leg portion with aperture 64 for receiving the lockset. The lockset comprises lock housing 56 with lock cylinder 60 positioned within. Lock cylinder 60 has a channel 66 scored into the body appropriately positioned to receive C-clip 68 once the cylinder and housing are inserted into aperture 64 and thereby secure the lockset to the pivot plate. Also shown is keyway 62 for receiving a key to open the lock.

Figure 9:
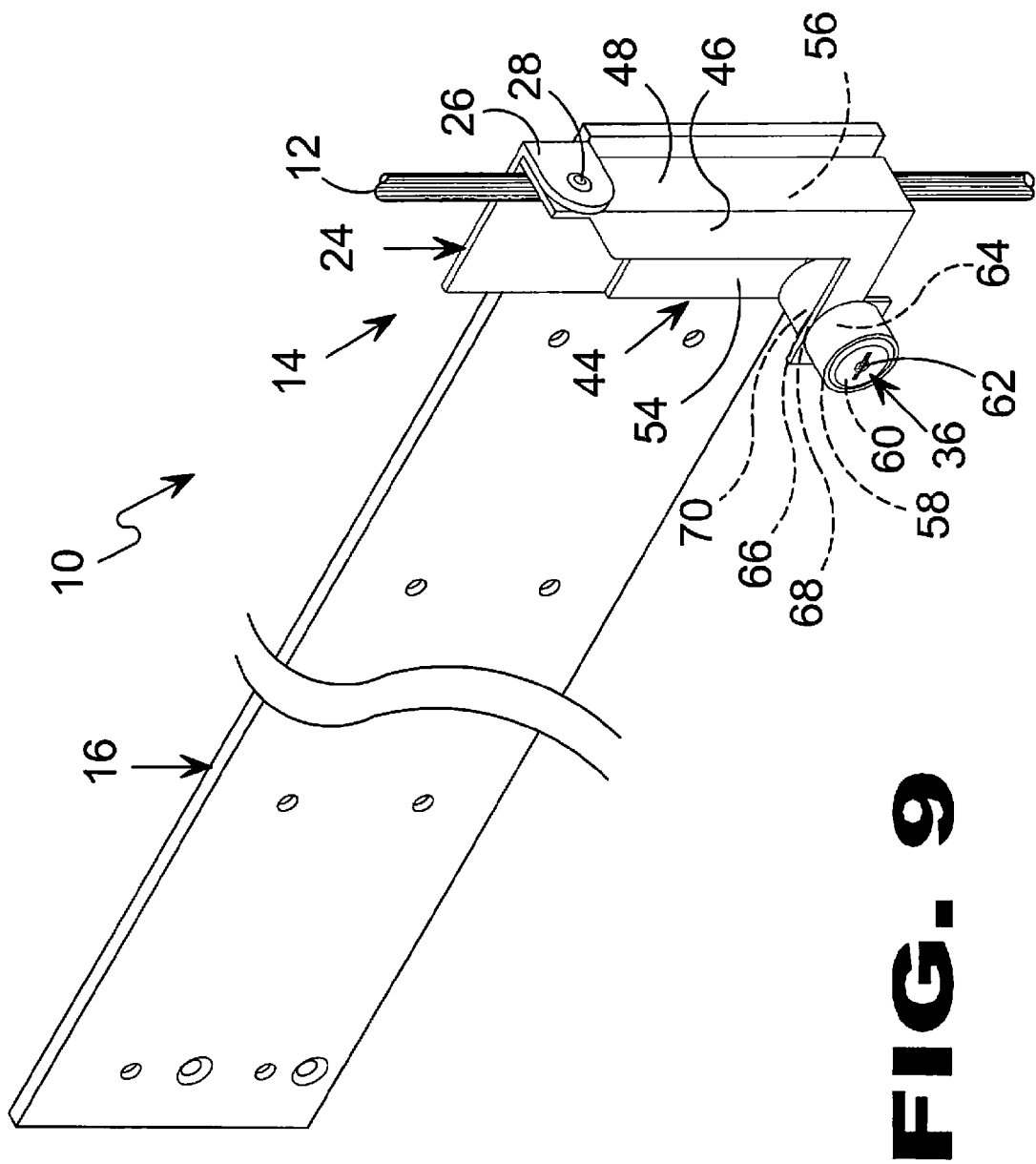
FIG. 9 is a perspective view of the present invention.

Referring to FIG. 9, shown a perspective view of the present invention. Shown is the anti-theft security lock 14 fastened to mounting plate 16 having mounting fasteners 20 for securing the plate to structure. the lock apparatus 14 comprising stationary plate 24 having flange 26 with pivot plate 44 fastened thereto via a fastener forming pivot point 28. Also shown are the stationary plate fastening apertures 30 with fasteners 32 and lock receiver 38 fastened to the stationary plate using fastener 40 having cavity 42 for retaining lock lugs 70. The pivot plate has walls 48, 46, and 52 forming channel 56 for securing an article therein when closed. Wall 52 extends into flange 54 which will cover the stationary plate mounting fasteners when closed preventing tampering. Wall 56 has an extending leg portion with aperture 64 for receiving the lockset. The lockset comprises lock housing 56 with lock cylinder 60 positioned within. Lock cylinder 60 has a channel 66 scored into the body appropriately positioned to receive C-clip 68 once the cylinder and housing are inserted into aperture 64 and thereby secure the lockset to the pivot plate. Also shown is keyway 62 for receiving a key to open the lock.

Figure 10:
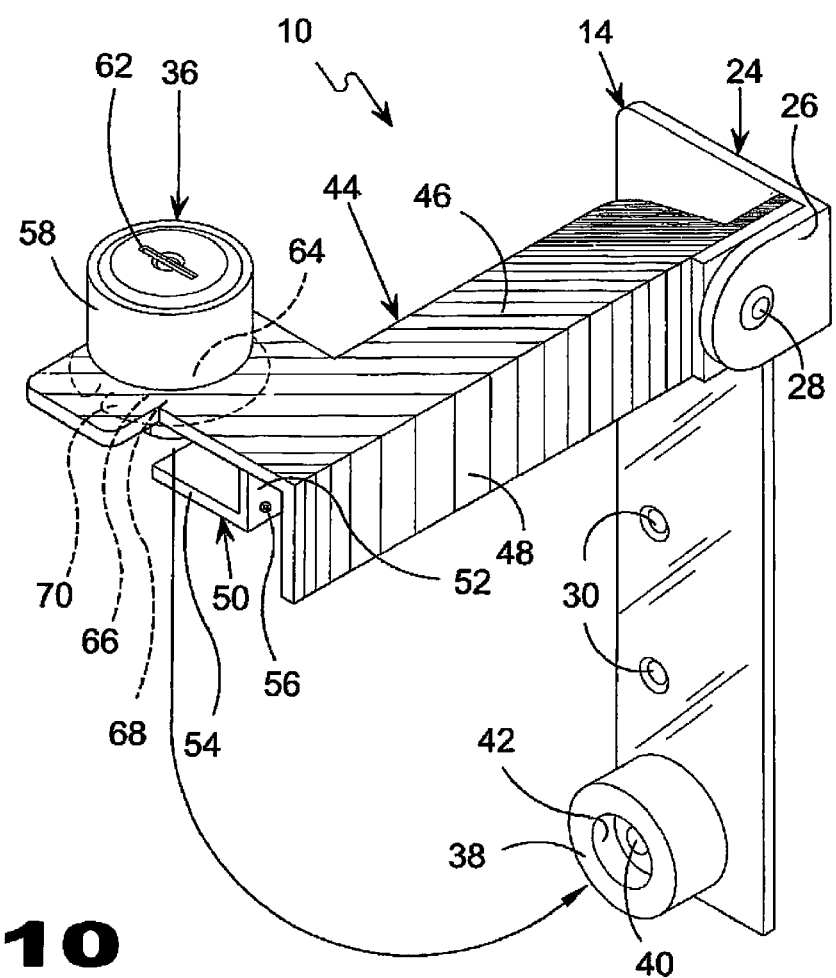
FIG. 10 is the theft prevention security device of the present invention for endoscopy probe cables and any cable or other device with each end larger than will fit through the lock channel when closed.

Referring to FIG. 10, shown is the theft prevention security device of the present invention for endoscopy probe cables and any cable or other device with each end larger than will fit through the lock channel when closed. Shown is the anti-theft security lock comprising stationary plate 24 having flange 26 with pivot plate 44 fastened thereto via a fastener forming pivot point 28. Also shown are the stationary plate fastening apertures 30 and lock receiver 38 fastened to the stationary plate using fastener 40 having cavity 42 for retaining lock lugs 70. The pivot plate has walls 48, 46, and 52 forming channel 56 for securing an article therein when closed. Wall 52 extends into flange 54 which will cover the stationary plate mounting fasteners when closed preventing tampering. Wall 56 has an extending leg portion with aperture 64 for receiving the lockset. The lockset comprises lock housing 56 with lock cylinder 60 positioned within. Lock cylinder 60 has a channel 66 scored into the body appropriately positioned to receive C-clip 68 once the cylinder and housing are inserted into aperture 64 and thereby secure the lockset to the pivot plate. Also shown is keyway 62 for receiving a key to open the lock.

Figure 11:
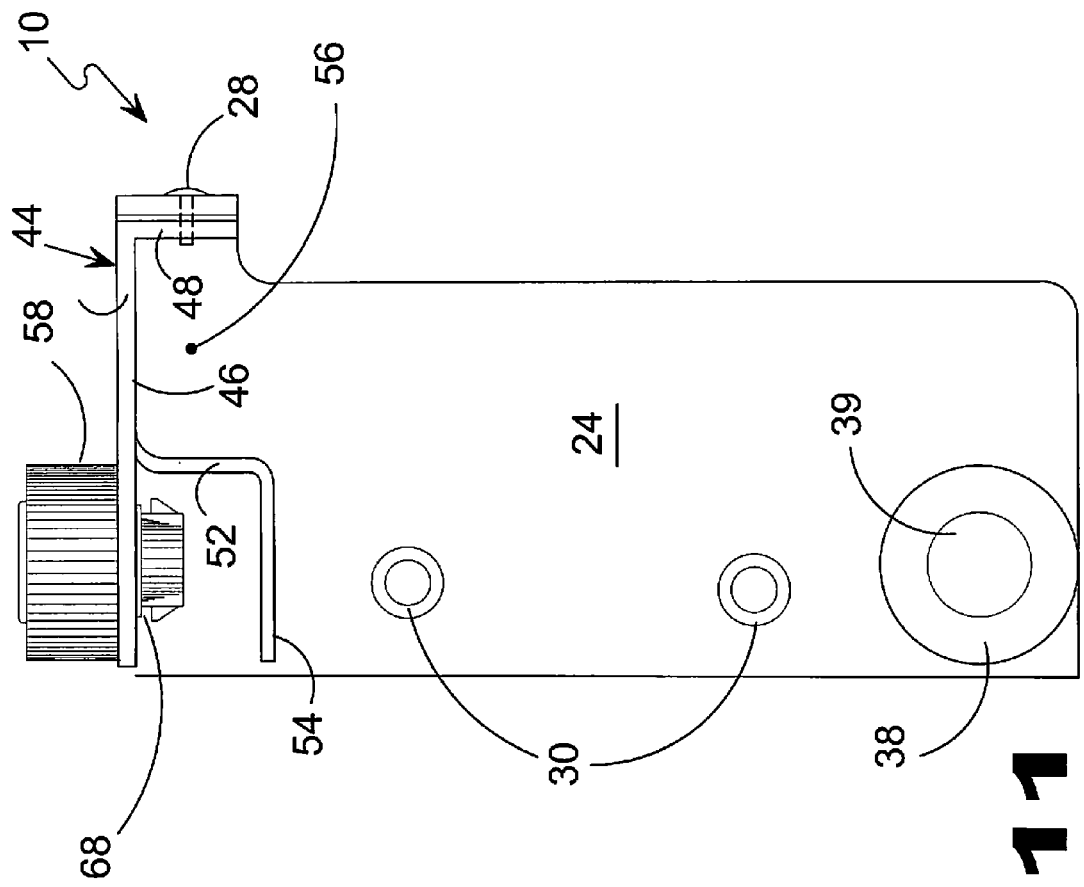
FIG. 11 is a frontal view of the present invention in an open position.

Referring to FIG. 11, shown is a frontal view of the present invention in an open position. The anti-theft security lock 10 provides locking apparatus 14 comprising stationary plate 24 and pivot plate 44 having walls forming channel 56 for securing article 12 therein. The lock receiver 38 is fastened to the stationary plate 24 and the lock housing 58 containing lock cylinder 60 and keyway 62 are secured to the pivot plate by securing the lock cylinder 60 having channel 66 to the pivot plate 44 using C-clip 68. Pivot plate 44 has flange 54 which cover stationary plate mounting fasteners 31 preventing tampering with the mounting fasteners.

Figure 12:
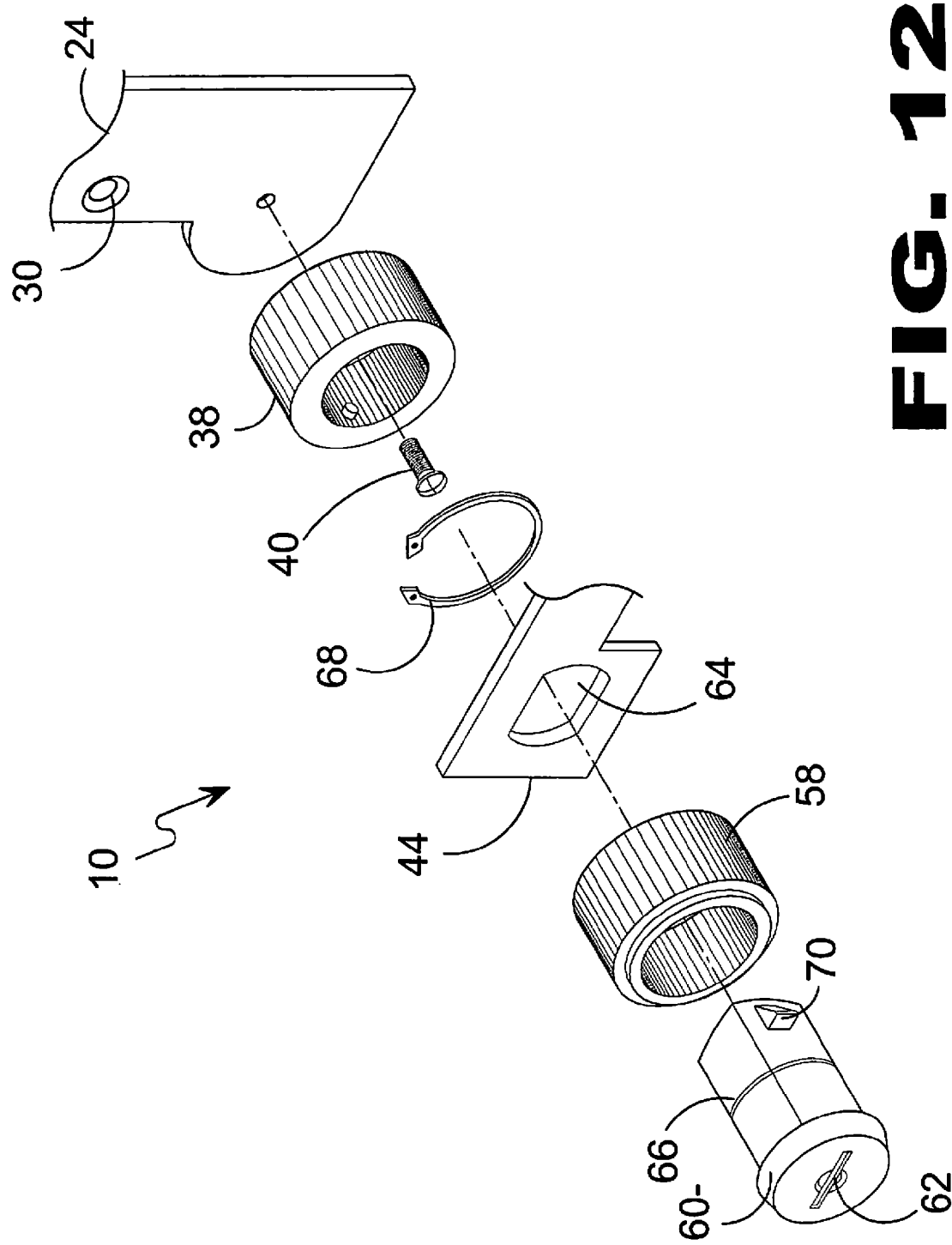
FIG. 12 is an exploded view of the anti-theft device.

Referring to FIG. 12, shown is an exploded view of the anti-theft device. Shown is the anti-theft device having a stationary plate 24 for fastening the device 10 to a structure. Fastened to the stationary plate 24 is lock receiver 38 fastened using lock receiver fastener 40. Lock apparatus 14 is secured to lock pivot-plate 44 by C-clip 68 inserted in C-clip channel 66 of lock cylinder 60. Once lock cylinder 60 is inserted into lock housing 58 and continues through pivot-plate lock aperture 64. Locking lugs 70 flair in lock lug receiver 42 preventing opening of the security device 10 without a key inserted into lock-cylinder keyway 62.

Figure 13:
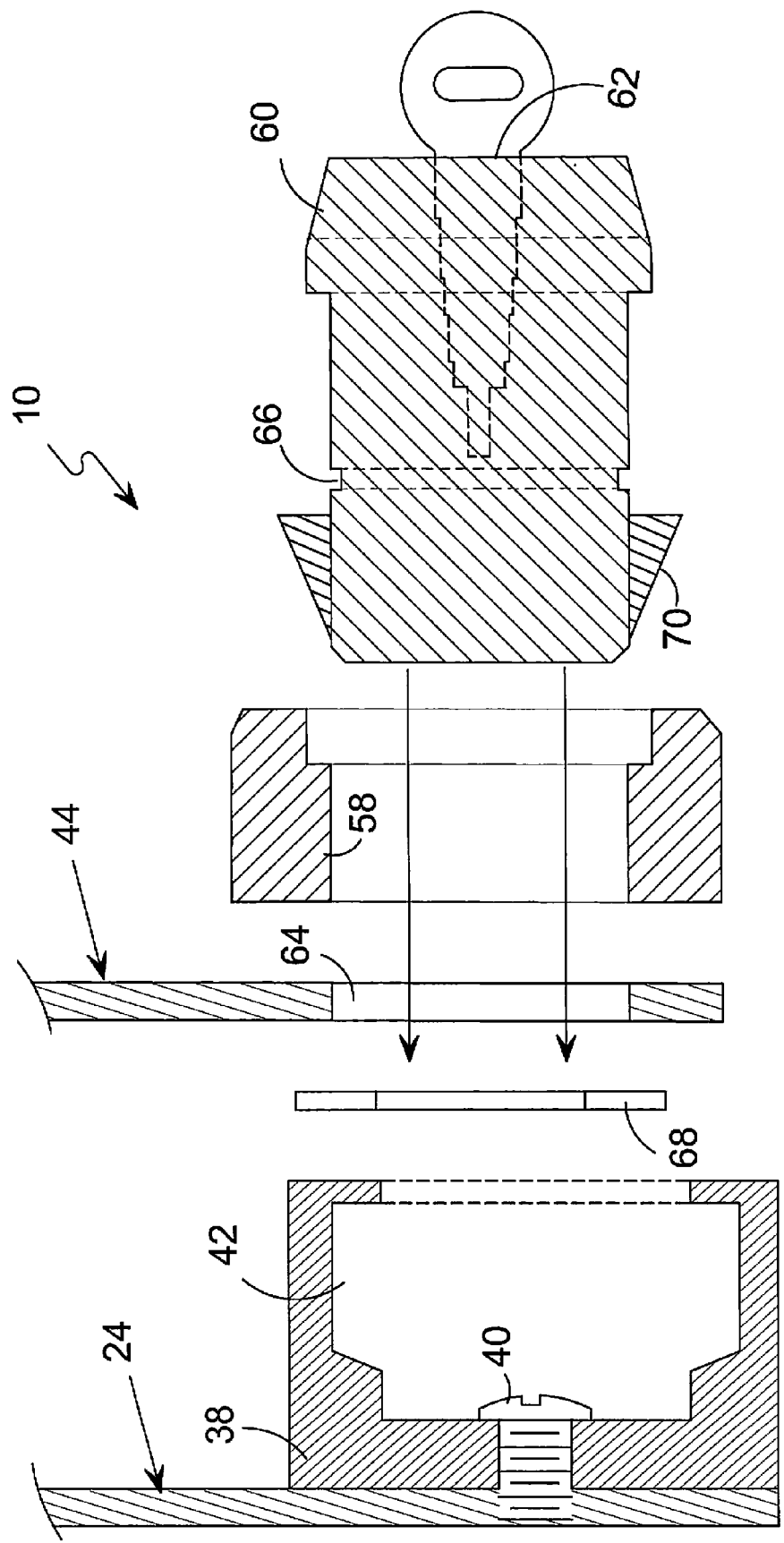
FIG. 13 is an exploded view of the anti-theft device.

Referring to FIG. 13, shown is an exploded view of the anti-theft device. Shown is the anti-theft device having a stationary plate 24 for fastening the device 10 to a structure. Fastened to the stationary plate 24 is lock receiver 38 fastened using lock receiver fastener 40. Lock apparatus 14 is secured to lock pivot-plate 44 by C-clip 68 inserted in C-clip channel 66 of lock cylinder 60. Once lock cylinder 60 is inserted into lock housing 58 and continues through pivot-plate lock aperture 64. Locking lugs 70 flair in lock lug receiver 42 preventing opening of the security device 10 without a key inserted into lock-cylinder keyway 62.

Figure 14:
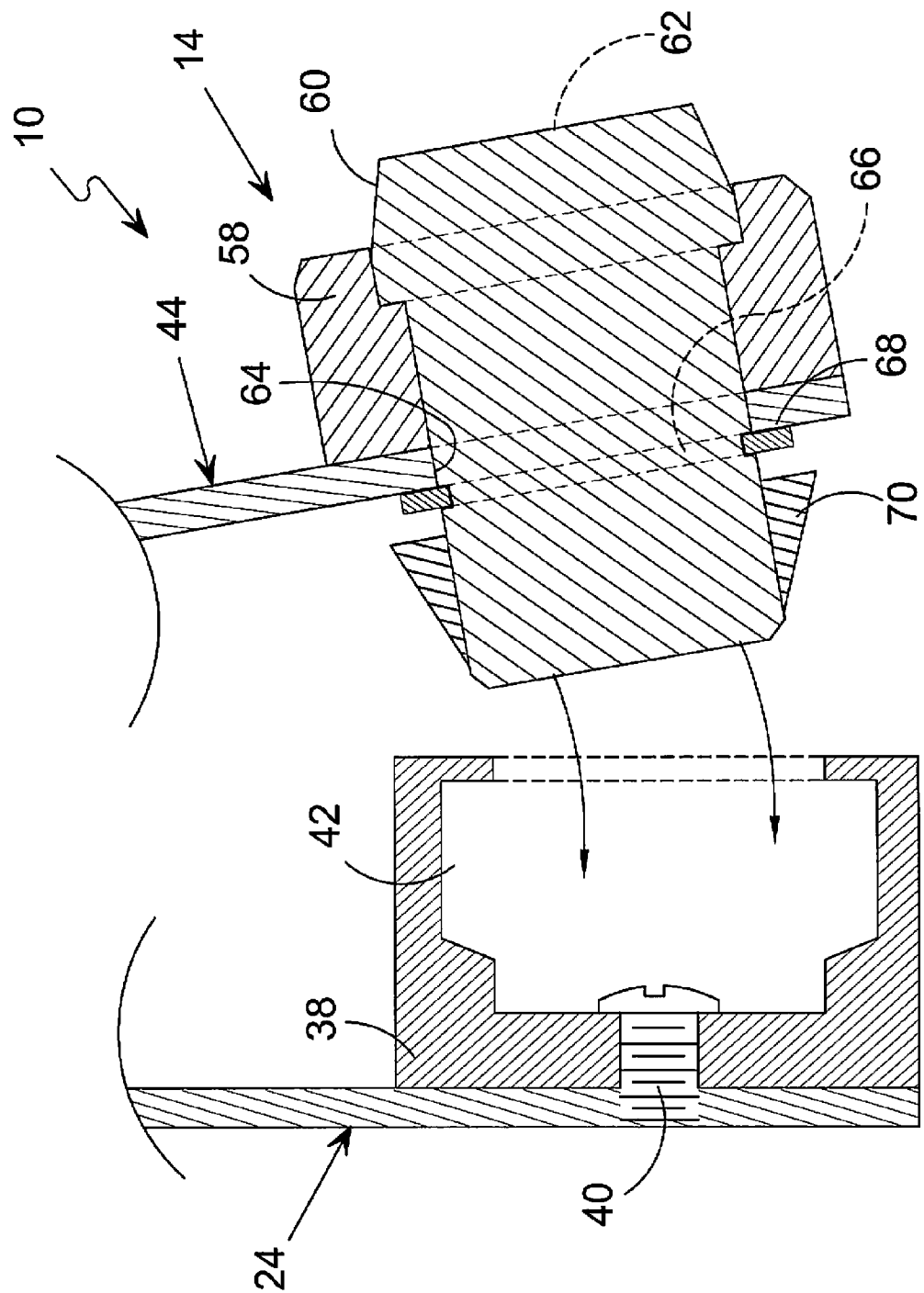
FIG. 14 is a sectional view of the lockset moving to closure.

Referring to FIG. 14, shown is a sectional view of the lockset moving to closure. Lock lugs 70 are tensioned so that a tangential pressure will move lugs 70 into lock cylinder 60 and therefore is enabled to moves to a locked state without the use of a key. Shown is lock apparatus 14 secured to lock pivot-plate 44 by C-clip 68 positioned in C-clip channel 66 of lock cylinder 60 moving into engagement with lock receiver 38.

Figure 15:
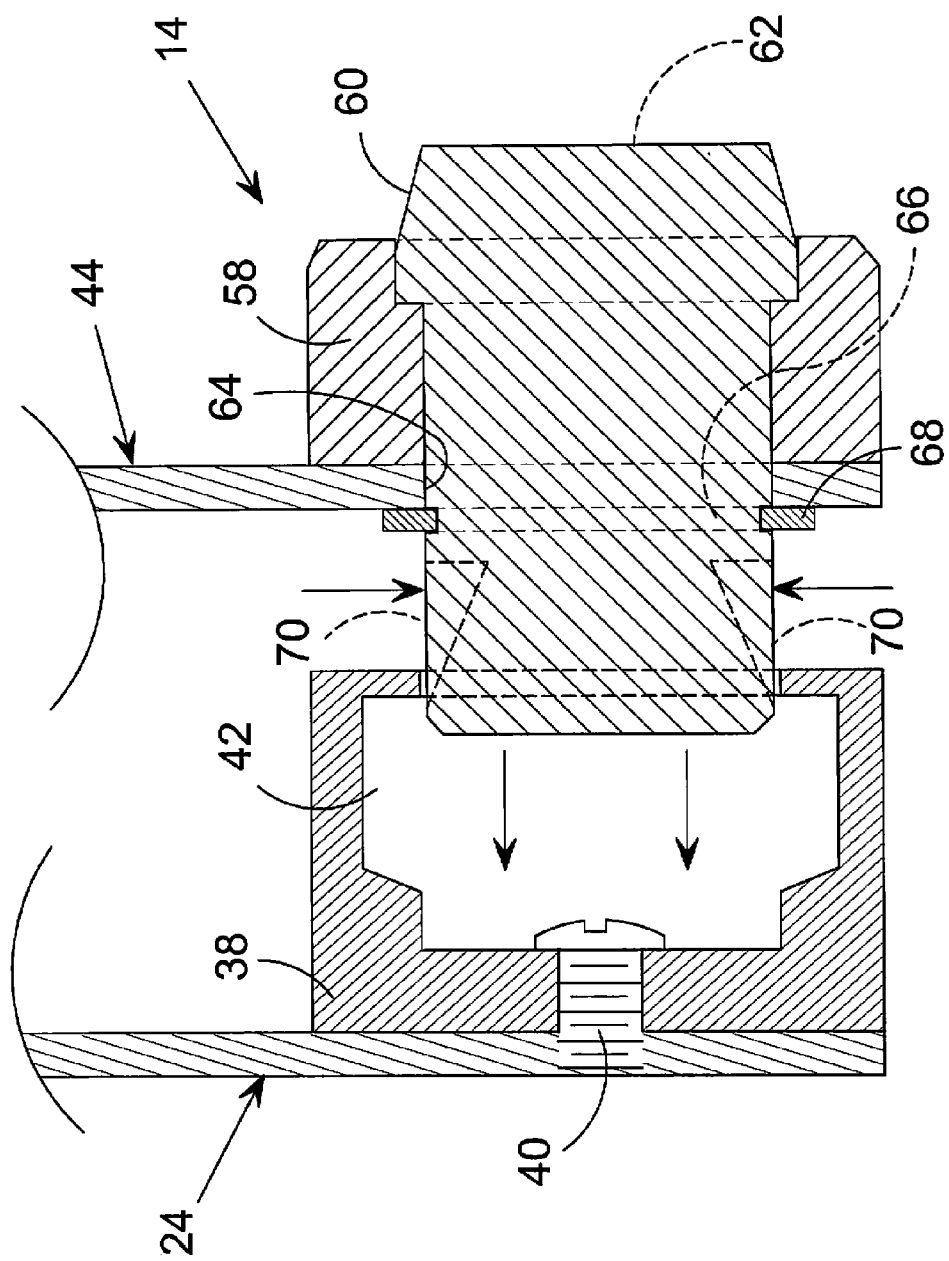
FIG. 15 is a sectional view of the lockset advancing to closure.

Referring to FIG. 15, shown is a sectional view of the lockset advancing to closure. Lock lugs 70 having engaged lock receiver 38 and subjected to tangential pressure will pivot into lock cylinder 60 and thereby enabled to move to a locked state without the use of a key. Shown is lock apparatus 14 secured to lock pivot-plate 44 by C-clip 68 positioned in C-clip channel 66 of lock cylinder 60 positioned with the lock receiver 38 bore.

Figure 16:
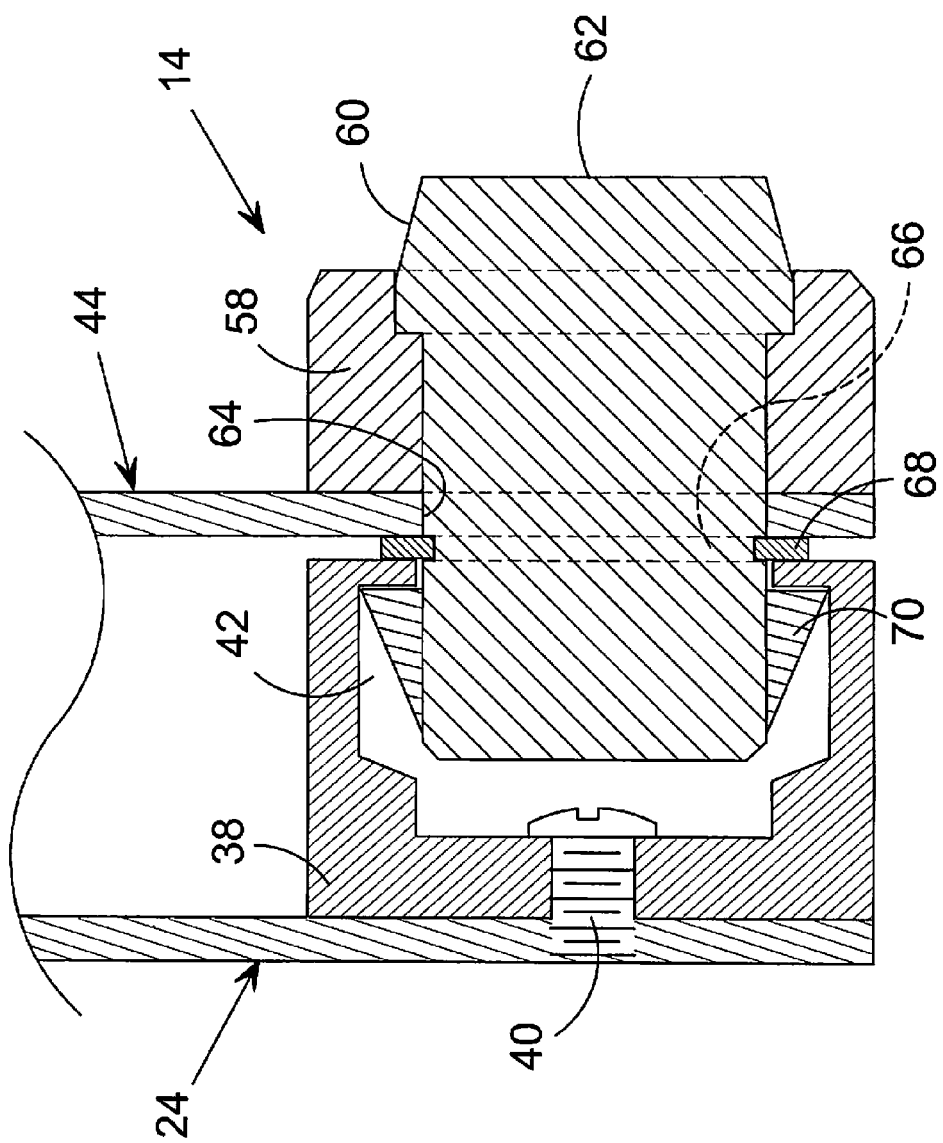
FIG. 16 is a sectional view of the present invention in a locked state.

Referring to FIG. 16, shown is a sectional view of the present invention in a locked state. Shown is a sectional view of the theft prevention security lock 10 of the present invention in a locked position. As illustrated, stationary plate 24 has lock receiver 38 fastened thereto using lock receiver fastener 40. Lock apparatus 14 is secured to lock pivot-plate 44 by C-clip 68 inserted in C-clip channel 66 of lock cylinder 60. Once lock cylinder 60 is inserted into lock housing 58 and through pivot-plate lock aperture 64, locking lugs 70 reside in lock lug receiver 42 preventing opening of the security device 10 without a key inserted into lock-cylinder keyway 62. While a key is necessary to gain access to an endoscopy probe that is locked within the device. Once the lock is unlocked, the device automatically locks without the use of a key when moved to the closed position.

Figure 17:
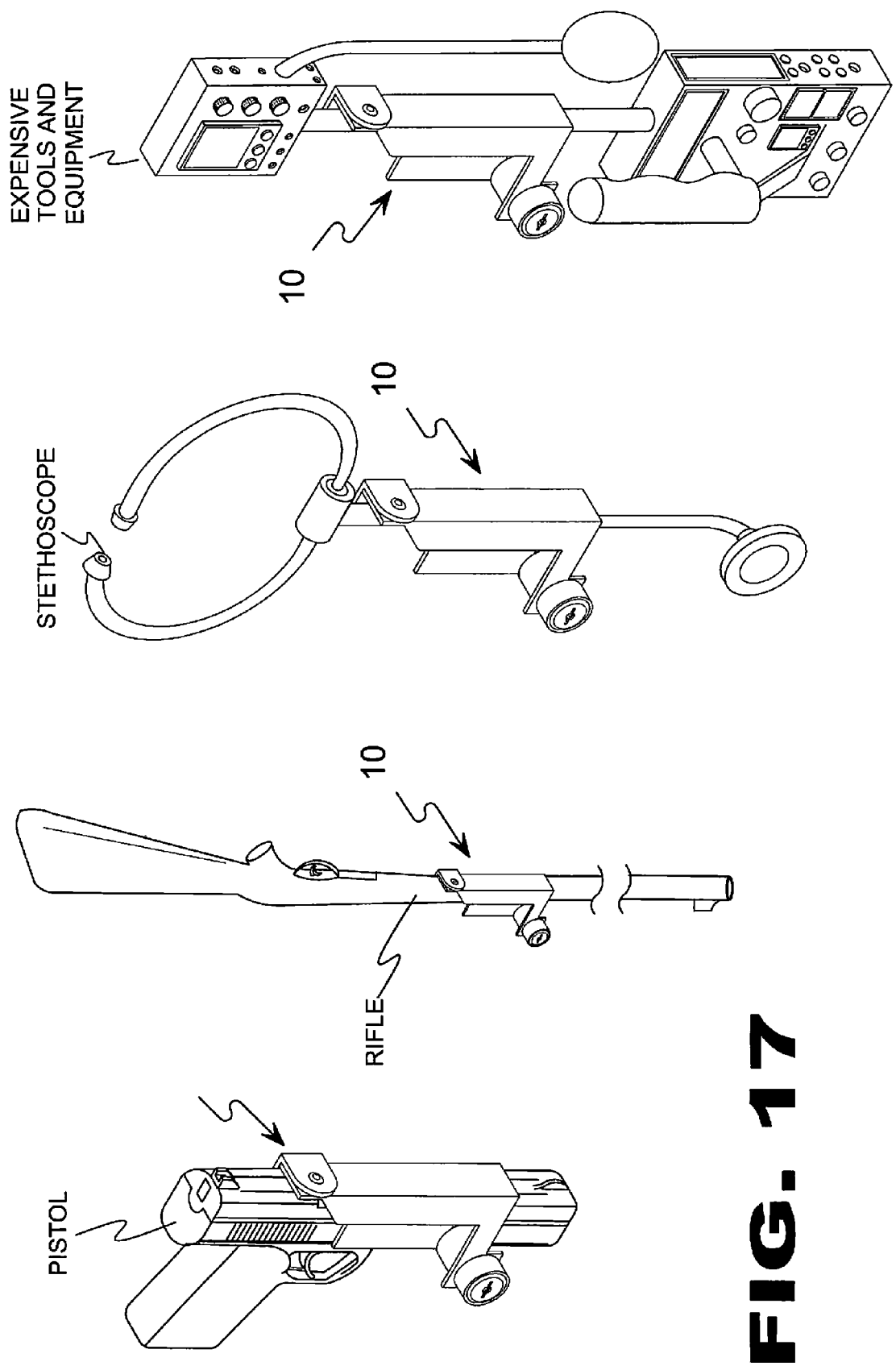
FIG. 17 is an illustrative view of the present invention for other uses.

Referring to FIG. 17, shown is an illustrative view of the present invention for other uses. Shown is the theft prevention security device of the present invention 10 having other devices with each end larger than will fit through the lock channel when closed, locked in a secure position. A key lock is provided and necessary to gain access to any device that would be locked within it.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention

The invention claimed is:

1. An anti-theft security lock comprising:
   a) a stationary plate mountable to a structure to prevent movement therefrom;
   b) a lock receiver mounted to the stationary plate;
   c) a pivot plate pivotally mounted to the stationary plate;
   d) a lockset mounted to the pivot plate; and
   e) the pivot plate having a U-shaped channel with a flange outwardly extending from one leg that covers the stationary plate mounting fasteners when the anti-theft lock is locked; and
   f) wherein said flange has an upper end positioned below an upper end of said stationary plate when the anti-theft lock is locked.

2. The anti-theft security lock of claim 1, wherein the lockset has pivotally attached tensioned locking lugs that pivot interiorly without the use of a key as the lockset is moved into engagement with the lock receiver.

3. The anti-theft security lock of claim 2, wherein the lock receiver has an entrance aperture of smaller diameter than the interior cavity whereby the tensioned locking lugs splay outwardly once past the entrance aperture therein preventing removal therefrom without the use of a key.

4. The anti-theft security lock of claim 1, wherein the channel formed by the lockingly engaged pivot plate and stationary plate form means for securing an article therein for articles having some article body portion of lesser cross sectional area bounded by body portions of greater cross sectional area so that the smaller body portion can be lockably held within the channel and the larger body portions prevent removal of the article from the anti-theft security lock.

5. The anti-theft security lock of claim 4, wherein the channel bore contains no mechanism for engaging any part of the held article which is held from removal due to the article having larger body portions outside of the lock channel.

6. The anti-theft security lock of claim 1, wherein the stationary plate is substantially planar with a flange outwardly extending at one end with an aperture in said flange for attaching the pivot plate thereto by means of a fastener.

7. An anti-theft security lock comprising:
   a) a stationary plate mountable to a structure to prevent movement therefrom;
   b) a lock receiver mounted to the stationary plate;
   c) a pivot plate pivotally mounted to the stationary plate;
   d) a lockset mounted to the pivot plate;
   e) the pivot plate having a U-shaped channel with a flange outwardly extending from one leg that covers the stationary plate mounting fasteners when the anti-theft lock is locked;
   f) wherein the stationary plate is substantially planar with a flange outwardly extending at one end with an aperture in said flange for attaching the pivot plate thereto by means of a fastener; and
   g) wherein the stationary plate has a lock receiver housing mounted on the other end and secured to the stationary plate by a fastener accessible only through the lock receiver housing entrance orifice.

8. The anti-theft security lock of claim 1, wherein said flange is substantially parallel with the stationary plate when closed and prevents access to the stationary mounting fasteners.

9. An anti-theft security lock comprising:
   a) a stationary plate mountable to a structure to prevent movement therefrom;
   b) a lock receiver mounted to the stationary plate:
   c) a pivot plate pivotally mounted to the stationary plate;
   d) a lockset mounted to the pivot plate; and
   e) the pivot plate having a U-shaped channel with a flange outwardly extending from one lea that covers the stationary plate mounting fasteners when the anti-theft lock is locked;
   f) wherein said flange is substantially parallel with the stationary plate when closed and prevents access to the stationary mounting fasteners; and
   wherein said flange extends from a base of a channel wall that is spaced apart from the other channel wall having a top wall section extending between the channel walls with said top wall having a leg portion with an aperture for mounting the lockset therein.

10. The anti-theft security lock of claim 9, wherein said lockset comprises a lock housing having a bore with a larger diameter portion and a smaller diameter portion so that the lip between the diameters supports the lock cylinder when positioned therein.

11. The anti-theft security lock of claim 10, wherein the lock cylinder has an exteriorly scored channel that is positioned so that when the lock cylinder is inserted into the lock housing arid through the top wall leg portion aperture a C-clip is inserted into the channel securing the lockset to the pivotal plate.

* * * * *